United States Patent [19]

Gilbard

[11] 4,269,197
[45] May 26, 1981

[54] METHOD OF MEASURING TEAR OSMOLARITY AND APPARATUS THEREFOR

[76] Inventor: Jeffrey P. Gilbard, Box 239, Vanderbilt Hall, 107 Ave. Louis Pasteur, Boston, Mass. 02115

[21] Appl. No.: 27,373

[22] Filed: Apr. 5, 1979

[51] Int. Cl.³ .............................................. A61B 10/00
[52] U.S. Cl. ................................. 128/763; 73/425.4 P
[58] Field of Search ................ 128/630, 760, 763–766, 128/233; 73/64.3, 425.4 P; 422/100; D24/55

[56] References Cited

U.S. PATENT DOCUMENTS 3,138,299  6/1964  Staunton .......................... 73/425.4 P

OTHER PUBLICATIONS

Mishima, Saiichi et al., "The Tear Flow Dynamics in Normal and in Kerato Conjunctivitis Sicca Cases", Amsterdam Excerpta Medica, 1971, pt. 2, pp. 1801–1805.
Gilbard, J. et al., "Osmolarity of Tear Microvolumes in Keratoconjunctivitis Sicca", Arch. Ophthalmology, vol. 76, Apr. 1978, pp. 677–681.

Primary Examiner—Robert W. Michell
Assistant Examiner—Francis J. Jaworski
Attorney, Agent, or Firm—Omri M. Behr

[57] ABSTRACT

A novel form of pipette has been developed for taking samples of tears in an eye, which is so constructed as to structure and size that it will not stimulate excess tear production thus giving rise to false readings. The novel pipette comprising a substantially L-shaped capillary tube drawn out at the shorter end thereof, which, in the use thereof, is touched to the tear strip of the eye to be examined.

5 Claims, 5 Drawing Figures

...

METHOD OF MEASURING TEAR OSMOLARITY AND APPARATUS THEREFOR

BACKGROUND OF THE INVENTION

In order to diagnose and treat the condition known as keratoconjunctivitis sicca (KCS), commonly known as "dry eye", it is useful to determine the osmolarity of the tears in the affected eye. It has been postulated that the condition of the eye is caused by a higher level of osmolarity in the tear fluid covering the eye than is generally desirable. In order to determine the level of the tear osmolarity, it is necessary to take samples of the tear from the eye itself. The volume of tear abstracted must be sufficient to carry out osmolarity measures by means which are well known in the art. On the other hand, the volume of liquid abstracted from the eye and the method of abstracting same must be such as to not stimulate the tear glands into provision of extra amounts of liquid at the moment of or during the sampling steps, which can lead to false readings.

Several approaches to this problem have been attempted and discussed by Applicant herein and co-workers in Arch Ophthalmol 96, 677, (1978). The samples in certain of these prior methods were so large as to raise serious questions of stimulation of the tear gland.

Mishima et al (Ophthalmology, Proceedings of the XXI International Congress, Mexico, DF, Mar. 8-14 1970; Amsterdam, Excerpta Medica, 1971, pt 2, pp 1801-1805) disclose and discuss a method wherein samples as small as 0.1 through 0.15 $\mu l$ are abstracted. This volume of sample is sufficiently small as to cause no problems of additional tear stimulation; however, the method suffers from certain practical problems.

In the method of Mishima there is utilized a small, straight pipette. A certain small quantity of oil is aspirated into the pipette, the tear sample is then abstracted and more oil is aspirated into the pipette to seal off the aspirated sample. Due to the very small size of the pipette utilized, practical difficulties have been encountered with the technique which may be due to the alteration of surface tension characteristics of the pipette by the oil which is aspirated in the first step. Further, since the technique of Mishima depends upon actual aspiration, problems relating to aspiration of air, contacting the eye, eliciting reflex tearing, and accidentally pulling out the tear strip of the sampled eye have been noted.

It was therefore believed desirable to develop an apparatus and method of utilizing same which maintains the highly desirable small volume requirements of Mishima without the practical problems which utilizing the technique brought about.

SUMMARY OF THE INVENTION

The apparatus utilized in the instant invention comprises a substantially L-shaped capillary tube having a continuous bore provided with a stem portion and a shorter tail portion. The tail portion is drawn out to provide a fine capillary having an internal diameter of about 0.05 mm to 0.2 mm and an outer diameter of between 0.1 mm through 0.5 mm. The length of the stem portion is not important; however, it has been found useful to provide the tail portion to be of approximately 1 cm in length. The tail portion has an internal bore diameter smaller than the internal bore diameter of said stem portion. This length, however, should in no way be considered as a critical aspect of the present invention.

In the operation of the invention the end of the tail portion of the pipette is touched to the lower tear film meniscus. The capillary action draws a volume of approximately 0.1 to 0.4 $\mu l$ of tear into the aforesaid tail portion of the capillary pipette. This volume is insufficient to stimulate tear flow and the mode of sampling is such as to avoid undesirable reflex action of the eye during the sampling process.

There is prepared a further capillary tube containing a suitable oil, for example immersion oil, said capillary tube being sealed at one end. The diameter of said capillary is not critical, however, it is desirable that it shall be sufficiently large to accommodate the end of the tail portion of the capillary pipette. Said end portion of said capillary pipette is introduced below the surface of the oil in said second capillary and the major portion of the sample of tear in the said tail portion is blown into the second capillary under the surface of the oil therein. The tear sample thus introduced into the oil-containing capillary can be stored for a reasonable amount of time and may be withdrawn as desired for determination of the osmolarity by freezing point depression utilizing commercially available osmometers by well known techniques. The sample of tear is withdrawn from the oil capillary reservoir by a reversal of the technique utilized for placing the tear sample therein.

The advantage of the present apparatus and its use over the prior art technique lies in the rapid and substantially reflexless abstraction of tear liquid from the sample eye, reserving the more time-consuming manipulation techniques for the bench where time and reflex action constitute no danger to the accuracy of the initial measurement.

DESCRIPTION OF THE PREFERRED EMBODIMENT

Figure 1:
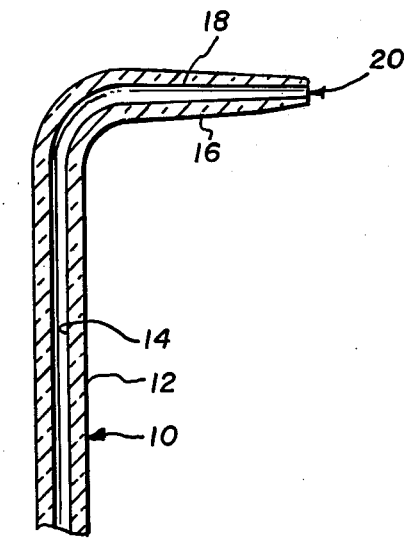
FIG. 1 is a cross-sectional view of a pipette utilizing the principles of the present invention.
Figure 2:
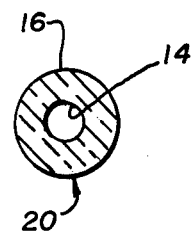
FIG. 2 is an end view of the tail opening of the pipette shown in FIG. 1.

I refer now to the Figures, and in particular to FIGS. 1 and 2, which show the pipette 10 utilized in the present invention. The pipette 10 comprises a stem portion 12 having a continuous bore 14 running therethrough connected to a tail portion 16 having a portion 18 of bore 14 running therethrough. The tail portion 16 is preferably drawn out to provide an end portion 20 which is bent to be generally perpendicular to said stem portion 12. The external diameter of the tail portion 16 is preferably between about 0.1 to 0.25 mm and the internal diameter of the bore 18 is preferably between about 0.05 mm to 0.2 mm. The tail portion 16 has no critical length, however, a length of the order of 1 cm has been found suitable. Similarly the length of stem portion 12 is not critical but preferably a length of approximately 4 to 5 cm has been found suitable.

Figure 5:
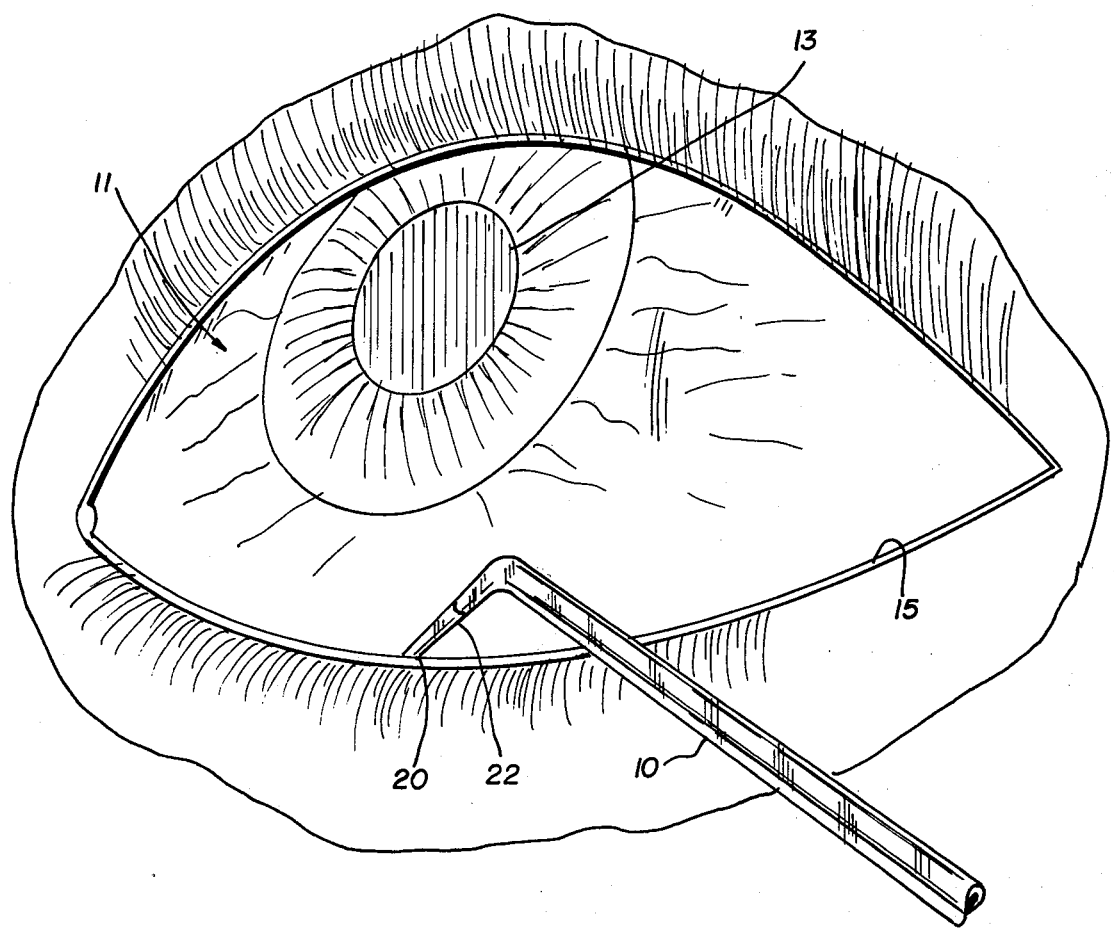
FIG. 5 is an enlarged pictorial representation of an eye during the sampling state showing the contacting of the capillary of FIG. 1 to the tear strip of the sample eye.

In operation, the pipette 10 is utilized after stabilizing the head of the patient to be sampled, visualizing the eye 11 with a slit beam biomicroscope, taking care not to shine a slit lamp light beam on the cornea 13. The subject is asked to look up and end 20 of pipette 10 is touched to the lower tear meniscus 15, whereby a sample tear drop 22 in the order of 0.1 to 0.4 µl enters bore 18 by capillary action. (See FIG. 5.)

Figure 3:
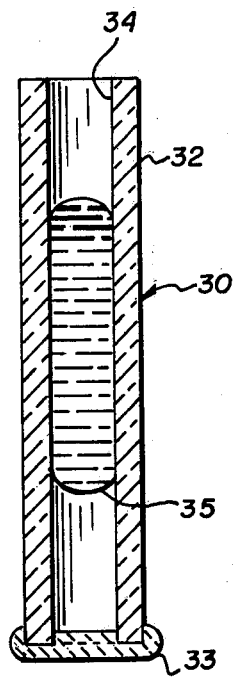
FIG. 3 is a cross-sectional view of the second oil-containing capillary utilized to store a tear sample.
Figure 4:
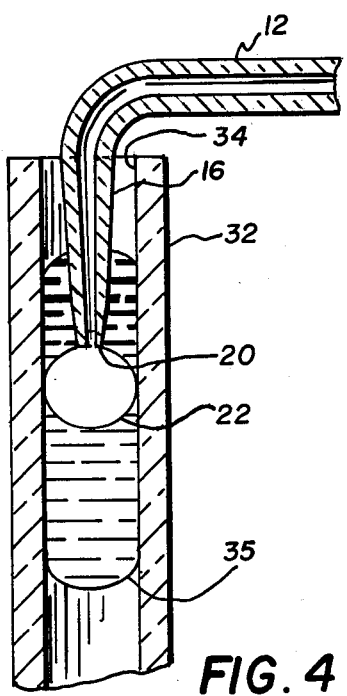
FIG. 4 is a cross-sectional view of a portion of the capillary shown in FIG. 3 with the tail portion of the capillary shown in FIG. 1 inserted therein just as the major portion of the tear sample is being blown out of said abstracting capillary into said oil reservoir of the storage capillary.

In the second step of the measurement process there is utilized a second capillary tube 30 (FIG. 3) having an outer wall 32 and a bore 34 therethrough. The inner diameter of bore 34 is greater than the outer diameter of the tail portion 18 of pipette 10. The second capillary tube 30 is filled with oil suitably an immersion oil 35, preferably Cargailles B, and one end thereof sealed, suitably with molding clay 33 or the like. End 20 of pipette 10, now containing the tear sample 22, is introduced below the surface of the oil 35 (FIG. 4). The pipette 10 is partially cleared by applying mild pressure, suitably by blowing through bore 14, whereby the tear sample forms a bubble 22 in oil column 35. It is desirable to remove pipette 10 from the interior of the oil 35 with a small amount of tear still maintained proximate to end 20 in bore 18. This procedure insures that the bubble 22 is not contaminated with air.

It has been found that oil-filled capillary tubes into which the tear sample has been introduced may be stored at ambient temperatures, that is to say between about 10° C. to 20° C., for not more than 48 hours, preferably not more than 24 hours without detectable change in osmolarity. The osmolarity of the tear sample may be measured by freezing point depression upon a commercially available osmometer capable of making measurements on samples as small as 0.1 µl. The accuracy of such instruments is of the order of ±0.76%.

When it is desired to make the measurement on the osmometer, a fresh pipette substantially identical in dimension and appearance with the originally utilized pipette is introduced under the surface of oil layer 35 and the tear sample 22 is removed therefrom by application of reduced pressure upon the bore 14 of the pipette 10. Again care should be taken that the entire portion of the tear sample 22 is not removed to avoid aspiration of oil.

The tear sample is then transferred from the pipette into the osmometer where the osmolarity is measured in accordance with procedures well known in the art.

I claim:

1. A substantially L-shaped pipette having a continuous bore therethrough, for collection of tear samples comprising:
   (a) a stem portion having an internal bore and
   (b) a tail portion, oriented generally perpendicular to said stem portion, said tail portion having an internal bore diameter of from about 0.05 mm to about 0.2 mm and an external diameter of from about 0.1 mm to about 0.25 mm wherein the open end of said tail portion is in the part of said tail portion most distant from said stem portion, said tail portion having an internal bore diameter smaller than the internal bore diameter of said stem portion.

2. The method of sampling tears from a patient without stimulating additional tear flow which comprises, touching the open end of the tail portion of the pipette of claim 1 to the lower tear meniscus of an eye of a patient, whereby a tear sample is drawn into said pipette by capillary action.

3. The method of storing a tear sample obtained from a patient comprising:
   (a) procuring said tear sample in accordance with the method of claim 2;
   (b) providing a capillary tube having an internal diameter greater than the external diameter of said tail portion;
   (c) inserting oil in said capillary tube;
   (d) introducing the open end of said tail portion of said pipette below the surface of said oil;
   (e) expelling the major portion of said tear sample from said pipette below the surface of said oil.

4. The method of sampling and storing tears from a patient without stimulating additional tear flow which comprises:
   (a) touching the open end of the tail portion of a pipette having a bore diameter of from about 0.05 mm to about 0.2 mm and an external diameter of from about 0.1 mm to about 0.25 mm to the lower tear meniscus of an eye of a patient to obtain a tear sample into said pipette bore by capillary action;
   (b) providing a capillary tube having an internal diameter greater than the external diameter of said tail portion;
   (c) inserting oil in said capillary tube;
   (d) introducing the open end of said tail portion of said pipette below the surface of said oil;
   (e) expelling the major portion of said tear sample from said pipette below the surface of said oil.

5. An apparatus for taking and storing samples of tears from a patient's eye without stimulating tear production, comprising a combination of:
   (a) a substantially L-shaped pipette having a stem portion and a tail portion with a continuous bore running therethrough, said tail portion being generally perpendicular to said stem portion and having a bore diameter smaller than said stem portion bore;
   (b) a capillary tube having an internal bore diameter greater than the external diameter of said tail portion and adapted to receive said tail portion therein;
   (c) means for sealing one end of said capillary tube; and
   (d) oil disposed with said capillary tube bore, said oil being adapted to suspend said tear drop therein.

* * * * *